(12) United States Patent
Khan et al.

(10) Patent No.: US 6,337,092 B1
(45) Date of Patent: Jan. 8, 2002

(54) COMPOSITION AND METHOD OF PREPARING MICROPARTICLES OF WATER-INSOLUBLE SUBSTANCES

(75) Inventors: Sheema Khan, Napean (CA); Gary W. Pace, Raleigh, NC (US)

(73) Assignee: RTP Pharma Inc., Durham, NC (US)

( * ) Notice: Subject to any disclaimer, the term of this patent is extended or adjusted under 35 U.S.C. 154(b) by 0 days.

(21) Appl. No.: 09/650,862

(22) Filed: Aug. 29, 2000

Related U.S. Application Data

(63) Continuation-in-part of application No. 09/277,726, filed on Mar. 29, 1999.
(60) Provisional application No. 60/079,809, filed on Mar. 30, 1998.

(51) Int. Cl.$^7$ ................................................. A61K 9/14
(52) U.S. Cl. ........................................ 424/489; 424/490
(58) Field of Search ................................. 424/489, 490

(56) References Cited

U.S. PATENT DOCUMENTS

| | | | |
|---|---|---|---|
| 5,091,187 A | 2/1992 | Haynes | 424/450 |
| 5,145,684 A | 9/1992 | Liversidge et al. | 424/489 |
| 5,298,262 A | 3/1994 | Na et al. | 424/489 |
| 5,326,552 A | 7/1994 | Na et al. | 424/4 |
| 5,336,507 A | 8/1994 | Na et al. | 424/489 |
| 5,340,564 A | 8/1994 | Illig et al. | 424/9 |
| 5,470,583 A | 11/1995 | Na et al. | 424/489 |
| 5,510,118 A | 4/1996 | Bosch et al. | 424/489 |
| 5,569,448 A | 10/1996 | Wong et al. | 424/9.45 |
| 5,851,275 A | 12/1998 | Amidon et al. | 106/148.1 |
| 5,858,410 A | 1/1999 | Muller et al. | 424/489 |
| 5,922,355 A * | 7/1999 | Parikh et al. | 424/489 |

FOREIGN PATENT DOCUMENTS

| | | |
|---|---|---|
| EP | 0 499 299 A2 | 8/1992 |
| EP | 0 580 690 B1 | 3/1996 |
| WO | WO 96/24332 | 8/1996 |
| WO | WO 97/14407 | 4/1997 |
| WO | WO 98/07414 | 2/1998 |
| WO | WO 99/29300 | 6/1999 |

OTHER PUBLICATIONS

[LSP4]La Fuma Polymery 1998 43 nr 2, 104–108 The role of water–soluble polymers at the solid/liquid etc.
Luckham Pestic. Sci., 1989, 25, 25–34 The Physical Stability of Suspension Concentrates with Particular etc.
Calvõr et al Pharm. Dev. Tech., 3(3), 297–205, 1998 Production of Microparticles by High Pressure etc.
Siekmann et al Pharm. Pharmacol Lett (1994) 3: 225–228Melt–homogenized solid lipid nanparticles etc.
Lourenco et al Int. J. Pharm. 138 (1996), 1–12 Steric stabilization of nanoparticles: size and surface properties.
Napper Polymeric Stabilizations of Colloidal Dispersions 1983.
Müller et al Emulsions and Nanosuspensions Chapter 9 1998 p 163.
Guzman et al 1088 J. Pharm. Sci 82 (1993 No. 5 pp 498–502 Formation and Characterization of Cyclosporine–Loaded–Nanoparticles.

\* cited by examiner

*Primary Examiner*—Jose' G. Dees
*Assistant Examiner*—Konata M. George
(74) *Attorney, Agent, or Firm*—Nixon & Vanderhye

(57) ABSTRACT

Pharmaceutical compositions comprising electrostatic and steric-stabilized sub-micron and micron-size stable microparticles of water-insoluble or poorly soluble drugs or other industrially useful insoluble compounds having diameters of about 0.05 to about 10 microns are described. The particles have phospholipid coated surfaces and are stabilized with a combination of charged surface modifier and block copolymer. The diameter of the particles is greater than about 50% but less than 100% of the diameter of particles comprising the poorly soluble drug and the phospholipid coated surfaces prepared by otherwise identical means in the absence of the combination of charged surface modifier and block copolymer. The charged surface modifier provides electrostatic stabilization and the block copolymer provides steric stabilization that minimize particle size growth caused by Ostwald ripening and particle aggregation and provides for small particle formation. The compositions of particles can be in the form of suspensions or powders that can be converted to other dosage forms.

12 Claims, No Drawings

COMPOSITION AND METHOD OF PREPARING MICROPARTICLES OF WATER-INSOLUBLE SUBSTANCES

This is a Continuation in Part of U.S. patent application Ser. No. 09/277,726 filed Mar. 29, 1999. This application claims benefit of provisional application Ser. No. 60/079,809 filed Mar. 30, 1998, the disclosure of which is hereby incorporated by reference.

This invention relates to compositions and processes that provide sub-micron and micron size stable particles of water-insoluble or poorly soluble drugs or other industrially useful insoluble compounds. The compositions of this invention include combinations of natural or synthetic phospholipids, a charged surface modifier such as a highly purified charged phospholipid, and a block copolymer coated or adhered onto the surfaces of the water insoluble-compound particles. The combination of charged surface modifier and block copolymer allows the formation and stabilization of the sub-micron and micron size compound particles. The particles are stabilized by the charged surface modifier which provides electrostatic stabilization, and by the block copolymer which provides steric stabilization. The combination of charged surface modifier and block copolymer stabilize these particles with respect to particle growth, aggregation or flocculation.

BACKGROUND OF THE INVENTION

There is a critical need in the pharmaceutical and other biological based industries to formulate water-insoluble or poorly soluble substances into formulations for oral, injectable, inhalation, ophthalmic, and other routes of delivery. Water insoluble substances are those having poor solubility in water, that is <5 mg/ml at physiological pH (6.5–7.4). Preferably their water solubility is <1 mg/ml, and more preferably <0.1 mg/ml. Water-insoluble or poorly soluble substances as used herein include water-insoluble or poorly soluble pharmaceutical compounds and water-insoluble or poorly soluble drugs.

It is desirable that a water-insoluble or poorly soluble substance be stable when formulated as a dispersion, for example as a dispersion in an aqueous medium such as water. It is also desirable that a formulation of a water-insoluble or poorly soluble substance be stable when formulated as a dispersion. Alternatively, a dry formulation of the substance such as a lyophilized or spray-dried solid form of the formulation can be desirable.

As used herein, "micro-" refers to the largest cross section or diameter such as that of a particle having a cross section or diameter of from nanometers to micrometers. Thus, microparticles, as used herein, refer to solid particles having a cross section or diameter of from nanometers to micrometers and are of irregular or non-spherical or substantially spherical shapes. Drug formulations containing these microparticles provide some specific advantages over unformulated and non-micronized drug particles which include improved oral bioavailability of drugs that are poorly absorbed from GI tract, development of injectable formulations that are currently available only in oral dosage form, less toxic injectable formulations that are currently prepared with organic solvents, sustained release of intramuscular injectable drugs that are currently administered through daily injection or constant infusion, and preparation of inhaled or ophthalmic formulation of drugs that otherwise could not be formulated for nasal/oral inhalation or ocular use.

Current technologies for delivering insoluble drugs as described in U.S. Pat. Nos. 5,091,188; 5,091,187; and 4,725,442 focus either on (a) coating small drug particles with natural or synthetic phospholipids or (b) dissolving the drug in a suitable lipophilic carrier and forming an emulsion stabilized with natural or semisynthetic phospholipids. One of the disadvantages of these formulations is that certain drug particles in suspension tend to grow larger over time because of the dissolution and reprecipitation phenomenon known as "Ostwald ripening" or particle growth. As the solvent or medium surrounding the particle becomes saturated with solute such as a drug, the larger particles grow and become even larger as seen, for example in Luckham, Pestic. Sci., (1999) 25, 25–34.

Another approach, as described in a series of patents uses cloud point modifier(s). In U.S. Pat. Nos. 5,298,262; 5,326,552; 5,336,507; 5,304,564 and 5,470,583 a poorly soluble drug or diagnostic agent has adsorbed on its surface both a cloud-point modifier and a non-crosslinked nonionic surfactant. The role of the cloud point modifier is to increase the cloud point of the surfactant such that the resulting nanoparticles are resistant to particle size growth upon heat sterilization at 121° C.

U.S. Pat. No. 5,922,355 discloses the preparation of submicron size particles of pharmaceutical or other water-insoluble or poorly water-insoluble substances using a combination of one or more surface modifiers/surfactants such as polaxomers, poloxamines, polyoxyethylene sorbitan fatty acid esters and the like together with natural or synthetic phospholipids. Particles so produced have a volume weighted mean particle size at least one-half smaller than obtainable using a phospholipid alone. Compositions so prepared are resistant to particle size growth on storage. Phospholipid and surface modifier(s) are adsorbed on to the surfaces of drug particles in sufficient quantity to retard drug particle growth, reduce drug average particle size from 5 to 100 micrometers to sub-micron and micron size particles by one or combination of methods known in the art, such as sonication, homogenization, milling, microfluidization, precipitation or recrystallization or precipitation from supercritical fluid, and maintain sub-micron and micron size particles on subsequent storage as suspension or solid dosage form. In U.S. Pat. No. 5,922,355, the second surface modifier may function to suppress Ostwald Ripening, to help maintain particle size, to increase storage stability, to minimize sedimentation, and to decrease the particle growth during lyophilization and reconstitution. The second surface modifier adheres or coats firmly onto the surface of water-insoluble drug particles, and modifies interfaces between the particles and the liquid in the formulations. It increases the interface compatibility between water-insoluble drug particles and the liquid, and it may possibly orient preferentially with hydrophilic portions projected into aqueous medium and with lipophilic portions strongly adsorbed at the water-insoluble drug particle surfaces.

In U.S. Pat. No. 5,922,355, the use of a surface modifier or combination of surface modifiers in addition to a phospholipid provides (i) volume weighted mean particle size values that are at least 50% and preferably about 50–90% smaller than what can be achieved using phospholipid alone without the use of a surfactant with the same energy input, and (ii) compositions resistant to particle size growth on storage.

DESCRIPTION OF THE INVENTION

The present invention focuses on submicron to micron size particles or microparticles coated with a natural phospholipid which particles are prepared using a combination of electrostatic and steric stabilization from at least one charged surface modifier and at least one block copolymer respectively. The growth in size of the particles, and hence their storage stability, is controlled by a combination of electrostatic and steric stabilizing materials.

In particular, this invention describes a pharmaceutical composition comprising electrostatic and steric-stabilized particles having diameters of about 0.05 to about 10 microns of a water-insoluble or poorly soluble drug, said particles having phospholipid coated surfaces and being stabilized with a combination of a charged surface modifier and a block copolymer, wherein the diameter of said particles is greater than about 50% but less than 100% of the diameter of particles comprising said poorly soluble drug and said phospholipid coated surfaces prepared by otherwise identical means in the absence of said combination of charged surface modifier and block copolymer, and wherein the charged surface modifier provides electrostatic stabilization and the block copolymer provides steric stabilization that minimize particle size growth caused by Ostwald ripening and particle aggregation and provides for small particle formation.

In addition, this invention describes a pharmaceutical composition comprising electrostatic and steric-stabilized particles having diameters of about 0.05 microns to about 10 microns of a water-insoluble or poorly soluble drug, the particles coated with a mixture of 0.01% to 50% wt naturally occurring phospholipids, 0.01 to 5.0% wt of a charged surface modifier and 0.01 to 20% wt of a block copolymer, wherein the diameter of said particles is greater than about 50% but less than 100% of the diameter of particles comprising said poorly soluble drug and said naturally occurring phospholipids prepared by otherwise identical means in the absence of both said charged surface modifier and said block copolymer, and wherein the charged surface modifier provides electrostatic stabilization and the block copolymer provides steric stabilization (against) that minimize particle size growth caused by Ostwald ripening and particle aggregation and provides for small particle formation.

In addition, this invention also describes a pharmaceutical composition comprising a powder of electrostatic and steric-stabilized particles having diameters of about 0.05 microns to about 10 microns of a water-insoluble or poorly soluble drug, the particles coated with a mixture of 0.01% to 50% wt naturally occurring phospholipids, 0.01 to 5.0% wt of a charged surface modifier and 0.01 to 20% wt of a block copolymer, wherein the diameter of said particles is greater than about 50% but less than 100% of the diameter of particles comprising said poorly soluble drug and said naturally occurring phospholipids prepared by otherwise identical means in the absence of both said charged surface modifier and said block copolymer, and wherein the charged surface modifier provides electrostatic stabilization and the block copolymer provides steric stabilization (against) that minimize particle size growth caused by Ostwald ripening and particle aggregation and provides for small particle formation Unlike U.S. Pat. No. 5,922,355, the current invention provides particles that do not exhibit a reduction in volume weighted mean particle size values that are at least 50% or smaller than what can be achieved using phospholipid alone without the use of a surfactant with the same energy input. In addition, the current application provides particles whose subsequent growth is minimized by the presence of the combination. These points are exemplified in the tables of data in the examples that follow hereinbelow.

The use of this particular combination of electrostatic and steric stabilizers in addition to a natural phospholipid is characterized by its ability to result in volume weighted mean particle size values that are smaller than what can be achieved using phospholipid alone without the use of a surfactant with the same energy input, and provide compositions resistant to particle size growth on storage. In order to achieve the advantages of the present invention it is necessary that the natural phospholipid and stabilizers all be present at the time of particle size reduction or precipitation.

Another aspect of the present invention includes free-flowing powders of formulations containing these microparticles of poorly soluble or insoluble drug substances such as particles of cyclosporin as well as solid dosage forms of these powders, for instance in the form of compressed tablets and the like. Surprisingly we have found that microparticle formulations exhibit enhanced stability as illustrated in the data that follows.

Although we do not wish to be bound by any particular theory, it appears that these surface modifiers generally, that is phospholipids and one or more charged surface modifiers and block copolymers, these both sometimes referred to herein as surface modifiers or surfactants, adsorb to the surfaces of drug particles, and (a) convert lipophilic to hydrophilic surfaces with increased steric hindrance/stability, and (b) possibly modify zeta potential of surfaces with more charge repulsion stabilization. The concentrations of surface modifiers used in the process described here are normally above their critical micelle concentrations (CMC). Hence the formation of sub-micron to micron size particles is facilitated by stabilization of the small particles as they are formed to prevent reaggregation.

Phospholipid and surface modifier(s) are adsorbed onto the surfaces of drug particles in sufficient quantity to retard drug particle growth, reduce drug particle average size from 5 to 100 $\mu$ to sub-micron and micron size by one or a combination of methods known in the art, such as sonication, homogenization, milling, microfluidization, precipitation or recrystallization or precipitation from supercritical fluid, and maintain sub-micron and micron size on subsequent storage as a suspension of particles or as a solid dosage form.

The formulations of particles prepared by this invention may be dried into powders, e.g., by lyophilization, fluid or spray drying, which powders can be resuspended or filled into capsules or converted into granules or tablets with the addition of binders and other excipients known in the art of tablet making.

By industrially useful insoluble or poorly soluble compounds we include biologically useful compounds, imaging agents, pharmaceutically useful compounds and in particular drugs for human and veterinary medicine. Water insoluble compounds are those having a poor solubility in water, that is less than 5 mg/ml at or near neutral pH of 5 to 8, although the water solubility may be less than 1 mg/ml and even less than 0.1 mg/ml.

Examples of some preferred water-insoluble drugs include immunosuppressive agents such as cyclosporins including cyclosporine (cyclosporin A), immunoactive agents, antiviral and antifungal agents, antineoplastic agents, analgesic and anti-inflammatory agents, antibiotics, antiepileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antiarrhythmics, antihypertensive agents, hormones, and nutrients. A detailed description of these and other suitable drugs may be found in *Remington's Pharmaceutical Sciences*, 18th edition, 1990, Mack Publishing Co. Philadelphia, Pa.

The phospholipid may be any naturally occurring phospholipid or mixtures of phospholipids, sometimes referred to herein as "commercial" phospholipids, such as egg or soybean phospholipid or a combination thereof. The phospholipid may be salted or desalted, hydrogenated or partially hydrogenated or natural semisynthetic or synthetic. Examples of commercially available phospholipids include but are not limited to egg phospholipids P123 (Pfanstiehl), Lipoid E80 (Lipoid); and hydrogenated soy phospholipids, Phospholipon 90H, and 100H (Natterman), and 99% pure egg and soy phosphatidyl choline (Avanti Polar Lipids). The amount of phospholipid present in the composition ranges from 0.01% to 50%, preferably from 0.05% to 20%.

Block copolymers used in the invention display a brush-like interfacial conformation and possible steric stabilization to the particles. Suitable block copolymers include polaxomers, such as Pluronic™ F68, F108 and F127, which are block copolymers of ethylene oxide and propylene oxide available from BASF; and poloxamines, such as Tetronic™ 908 (T908, T707, T909, T1107 and T1307), which are tetrafunctional block copolymers derived from sequential addition of ethylene oxide and propylene oxide to ethylenediamine available from BASF; TritonTM™ X200, which is an alkyl aryl polyether sulfonate, available from Rohm and Haas. In a preferred aspect of the invention, when free-flowing formulations are desired, the block copolymer will itself be a powder. The amount of block copolymer is between 0.01% and 20%, preferably from 0.1% to 10%.

The charged surface modifier(s) used in the present invention are highly purified phospholipids either isolated from natural products or prepared synthetically. For example, commercially available phosphatidylcholine contains a small percentage of charged phosphalides such as phosphatidyl glycerol, phosphatidyl inosite, phosphatidyl serine and phosphatidic acid and its salts. Other charged phospholipids include palmitoyl-oleyl-phosphatidyl-glycerol (POPG) and dimiristoyl phosphatidylglycerol sodium salt (DMPG). Combinations of charged phospholipids may be used. These materials are present in relatively small amounts and serve to allow smaller particle formation and inhibit aggregation. The amount of charged phospholipids ranges from 0.01% to 5.0% and preferably from 0.05% to 1.0%.

It is thought that some of the functions of the combination of surface modifiers in this invention are (a) to suppress the process of Ostwald Ripening and thereby maintain the particle size, (b) to increase the storage stability, minimize agglomeration and sedimentation, and decrease the particle growth during lyophilization and reconstitution; (c) to adhere or coat onto the surfaces of water-insoluble drug particles and thereby modify the interfaces between the particles and the liquid in resulting formulations; (d) to increase the interface compatibility between water-insoluble drug particles and the liquid; and (e) possibly to orienting themselves preferentially with their hydrophilic portion directed or protruding into the aqueous solution and their lipophilic portion strongly adsorbed at the water-insoluble drug particle surfaces; and (f) to prevent aggregation of the small particles into clumps or aggregates as they are being formed using size reducing equipment or precipitation, such aggregates appearing in particle size measurement apparatus outputs as larger particles.

Considerable variations in the identities and types of charged surface modifier and especially the block copolymer are expected. The variations are anticipated to depend on the physical and chemical properties of the drug or active agent selected because the surface properties of small particles of different drugs are likely to be different. The most advantageous agents for an insoluble drug will be apparent as a result of empirical tests that can identify the phospholipid/charged surfactant/steric stabilizer system or combination that will provide initially desired microparticle size and microparticle size stability on storage over time. Such tests can include solubility and chemical compatibility evaluations, factorial design experiments, preliminary small scale formulation preparations, particle size analysis, pH analysis, temperature profiling, phase compatibility analysis, calorimetry, thermal analysis, spectroscopic analysis, Xray diffration analysis, short and long term stability evaluation, optical analysis, microscopic analysis, and other tests.

Various procedures can be used to produce these stable sub-micron and micron size microparticles. An example of such a procedure comprises the steps of mixing or premixing an insoluble substance such as a drug with phospholipid, charged surface modifier or stabilizer, and block copolymer or steric stabilizer followed by a particle size reduction step employing energy input such as sonication, milling, homogenization, microfluidization, and the like. Another example comprises the precipitation of a water insoluble or poorly water soluble substance from a solution using anti solvent in the presence of phospholipid, charged surface modifier or stabilizer, and block copolymer or steric stabilizer. Precipitation of drug from solvent can be done in the presence of the phospholipid and surfactant(s). Mannitol, other disaccharides, and other agents and excipients may be added to adjust the final formulation to isotonicity. Formulation stabilizing aids such as sugars can be added to stabilize the dispersions of microparticles during drying, for example during lyophilization or spray drying.

Unless otherwise specified, all parts and percentages reported herein are weight per unit volume (w/w), in which the volume in the denominator represents the total volume weight of the system. Diameters of dimensions are given in millimeters (mm=$10^{-3}$ meters), micrometers ($\mu$m=$10^{-6}$ meters), nanometers (nm=$10^{-9}$ meters) or Angstrom units (=0.1 nm). Volumes are given in liters (L), milliliters (mL= $10^{-3}$ L) and microliters ($\mu$L=$10^{-6}$L). Dilutions are by volume. All temperatures are reported in degrees Celsius. The compositions of the invention can comprise, consist essentially of or consist of the materials set forth and the process or method can comprise, consist essentially of or consist of the steps set forth with such materials.

The invention is further explained with reference to the following preferred embodiments. The following general procedure was used for the examples; exceptions are noted.

Preparation of Premix

Commercial phospholipid, mannitol, charged surface modifier and block copolymer were first mixed with water using a hand mixer. The drug was added afterwards to the mixture, and mixed for 10 min to 30 min at room temperature. In the case of cyclosporine, the pH was adjusted to 7.5–8.0 using 1N NaOH, and the premix was cooled to 12° C. using an ice bath. The batch size for cyclosporin was 200 g, for ursodiol 50 g, and for fenofibrate 200 g.

Processing Conditions

The premix was processed at a constant temperature and pressure by using high-pressure instrumentation that subjects the formulation to shear, cavitation, impact, and attrition, that is in either a microfluidizer or a homogenizer.

A "pass" is defined as one cycle of the formulation through the different elements of the processing machine. The "pass" or cycle for each machine is as follows:

Avestin C-50 and C-5: Formulation is placed in an inlet reservoir, then passes to the homogenization valve, then next through a heat exchanger, then back to the inlet reservoir. It is the homogenization valve that subjects the formulation to the forces of shear, cavitation, impact and attrition.

| Formulation type | Processing Machine | Total Passes at Operating Pressure | Average Pressure (kPsi) | Average Temperature (° C.) |
|---|---|---|---|---|
| Cyclosporine | Avestin C-50 homogenizer | 200 | 18 | 10 |
| Ursodiol | Avestin C-5 homogenizer | 100 | 18 | 13 |
| Fenofibrate | Microfluidizer M11OH | 50 | 18 | 5 |

M110H: The formulation is first put through 20 passes of a bypass loop which is defined as follows: from inlet reservoir to auxiliary processing module to heat exchanger then back to inlet reservoir. The resulting formulation is then put through an interaction chamber loop which is defined as follows: inlet reservoir to auxiliary processing module to interaction chamber to heat exchanger then back to inlet reservoir. It is in the interaction chamber where the formulation is subject to the forces of shear, cavitation, impact and attrition.

Following processing, each formulation was collected and placed in vials for stability testing. "MP" indicates microparticles falling within the range of 0.05 to 10 microns.

The five different types of stability tests are described as follows:

| Stability Test | Description |
|---|---|
| 4° C. | Sample stored at 4° C. (temperature controlled) |
| 25° C. | Sample stored at 25° C. (temperature controlled, 60% relative humidity) |
| 25° C. (2) | Sample stored at ambient room temperature -cyclosporine only |
| 40° C. | Sample stored at 40° C. (temperature controlled) |
| Shaking | Sample laid down on its side on a shaking table at ambient room temperature. The shaking speed was at 100 rpm–110 rpm. |
| Thermal Cycling | One cycle defined as follows: sample stored at 4° C. for 2–4 days, then at 40° C. for 2–4 days. |

EXAMPLE 1

Effect of Steric and Charged Surface Modifiers on Particle Size Reduction

These experiments show that in the presence of phospholipid a combination effect of steric and charged stabilizers gives a smaller terminal particle size than by using either alone. In all cases, the total weight percent of surface modifiers (commercial phospholipid, block copolymer, charged surface modifier) is kept constant. Data are displayed in Tables 1.1, 1.2, and 1.3.

TABLE 1.1

MP Cyclosporine data (5% w/w micronized cyclosporine, 5.5% Mannitol) 200 g batches, processed on homogenizer Avestin C-50

| Sample | w/w % Lipoid E80 | w/w % DMPG | w/w % Pluronic F68 | # passes | Particle size (microns) |
|---|---|---|---|---|---|
| 1 | 10 | 0 | 0 | 209 | 2.62 |
| 2 | 9.5 | 0.5 | 0 | 217 | 1.20 |
| 3 | 9.0 | 0 | 1.0 | 177 | 1.77 |
| 4 | 8.7 | 0.45 | 0.95 | 210 | 1.08 |

TABLE 1.2

MP Ursodiol data (10% w/w Ursodiol, 5.5% Mannitol) 50 g batches, processed on homogenizer Avestin C-5

| Sample | w/w % Lipoid E80 | w/w % DPPE | w/w % Tetronic 908 | # passes | Particle size (microns) |
|---|---|---|---|---|---|
| 1 | 2.4 | 0 | 0 | 127 | 1.36 |
| 2 | 1.6 | 0 | 0.8 | 107 | 1.15 |
| 3 | 2.0 | 0.4 | 0 | 106 | 1.34 |
| 4 | 1.41 | 0.28 | 0.72 | 102 | 1.06 |
| 5 | 0 | 0.4 | 2.0 | 104 | 1.37 |

TABLE 1.3

MP Fenofibrate data (10% w/w Fenofibrate, 5.5% Mannitol)
200 g batches, processed on Microfluidizer M110H

| Sample | w/w % Lipoid E80 | w/w % DMPG | w/w % Poloxamer 407 | # passes | Particle size (microns) |
|---|---|---|---|---|---|
| 1 | 4.0 | 0 | 0 | 70 | 0.95 |
| 2 | 3.0 | 0 | 1.0 | 70 | 0.86 |
| 3 | 3.6 | 0.4 | 0 | 70 | 0.85 |
| 4 | 2.77 | 0.31 | 0.92 | 70 | 0.82 |

As can be seen from the data in Table 1.2, comparing lines 1 and 4 and in contrast to the invention disclosed in U.S. Pat. No. 5,922,355, the use of charged phospholipid DPPE (defined in Table 1 below) together with block copolymer Tetronic 908 provides a composition with particle size that is not at least 50% smaller than the particle size of the composition prepared in the absence of DPPE and Tetronic 908.

As can be seen from the data in Table 1.3, comparing lines 1 and 4 and in contrast to the invention disclosed in U.S. Pat. No. 5,922,355, the use of charged phospholipid DPMG (defined in Table 1 below) together with block copolymer Poloxamer 407provides a composition with particle size that is not at least 50% smaller than the particle size of the composition prepared in the absence of DPMG and Poloxamer 407.

The data for cyclosporine, ursodiol and fenofibrate show the particle size reduction is maximal in phospholipid coated microparticles in the presence of charged surface modifier and a block copolymer.

EXAMPLE 2

Effect of the Presence of Steric and Charged Stabilizers on the Rate of Particle Size Reduction.

As the formulation passes through the homogenizer, the average diameter of the formulated particles reduces in magnitude. An empirical relation has been found that relates the average diameter to the pass number:

Average diameter=K/(pass number)$^a$

The above equation can also be used to determine how many passes it takes for the average diameter to reduce to 1 micron:

# of passes to reach 1 micron=$(K)^{1/a}$.

The data in Tables 2.1 and 2.2 demonstrate that steric and charged stabilizers improve the rate of particle formation.

In Table 2.1 comparing line 4 with lines 1, 2, and 3, and in Table 2.2 comparing line 4 with lines 1, 2, 3, and 5, the data for ursodiol and fenofibrate show the rate of particle size reduction is maximal in the production of phospholipid coated microparticles in the presence of charged surface modifier and a block copolymer.

TABLE 2.1

MP Fenofibrate data (10% w/w Fenofibrate, 5.5% Mannitol)
Rate of particle size reduction - 200 g
batches on the Microfluidizer M110H

| Sample | w/w % Lipoid E80 | w/w % DMPG | w/w % Poloxamer 407 | Calculated # passes for 1 micron* |
|---|---|---|---|---|
| 1 | 4.0 | 0 | 0 | 44 |
| 2 | 3.0 | 0 | 1.0 | 33 |
| 3 | 3.6 | 0.4 | 0 | 37 |
| 4 | 2.77 | 0.31 | 0.92 | 27 |

*For Fenofibrate, the total pass number is the calculated value plus 20 passes of the formulation using the bypass loop.

TABLE 2.2

MP Ursodiol data (10% w/w Ursodiol, 5.5% Mannitol)
Rate of particle size reduction - 50 g batches
on the Avestin C5 homogenizer

| Sample | w/w % Lipoid E80 | w/w % DPPE | w/w % Tetronic 908 | Calculated # passes for 1 micron |
|---|---|---|---|---|
| 1 | 2.4 | 0 | 0 | 305 |
| 2 | 1.6 | 0 | 0.8 | 158 |
| 3 | 2.0 | 0.4 | 0 | 261 |
| 4 | 1.41 | 0.28 | 0.72 | 134 |
| 5 | 0 | 0.4 | 2.0 | 230 |

EXAMPLE 3

Effect of Steric and Charged Surface Modifiers on Particle Stability.

The data in Tables 3.1 to 3.10 demonstrate the combination of charged phospholipid and block copolymer provide stability against Ostwald ripening and aggregation of the particles in the formulations.

The data in Table 3.1 relate to the drug cyclosporine. The combination of the effect of steric and electrostatic stabilizers provides best stability and prevents or minimizes particle growth due to both Ostwald ripening and particle aggregation.

Minimization of particle size growth is demonstrated in the data of Table 3.1. While the invention disclosed in U.S. Pat. No. 5,922,355 provides compositions that are resistant to particle size growth on storage, the current invention provides compositions in which the combination of charged phospholipid and block copolymer minimizes particle growth due to both Ostwald ripening and particle aggregation. This is demonstrated in Table 3.1 for cyclosporin comparing line 4 (Lipoid E80 plus DMPG plus Pluronic F68) with lines 1 (Lipoid E80 alone), line 2 (Lipoid E80 plus DMPG), and 3 (Lipoid E80 plus Pluronic F68).

The data in Table 3.2 relate to the drug ursodiol. The combination of the effect of steric and electrostatic stabilizers provides best stability and prevents or minimizes particle growth due to both Ostwald ripening and particle aggregation.

Minimization of particle size growth is demonstrated in the data of Table 3.2. While the invention disclosed in U.S. Pat. No. 5,922,355 provides compositions that are resistant to particle size growth on storage, the current invention provides compositions in which the combination of charged phospholipid and block copolymer minimizes particle growth due to both Ostwald ripening and particle aggregation. This is demonstrated in Table 3.2 for ursodiol comparing line 4 (Lipoid E80 plus DPPE plus Tetronic 908) with lines 1 (Lipoid E80 alone), line 2 (Lipoid E80 plus Tetronic 908), and 3 (Lipoid E80 plus DPPE).

With respect to the data in Table 3.2, particularly lines 1 and 4 relevant to storage at 4° C. of a composition containing Ursodiol, the use of charged phospholipid DPPE (see Table 1) together with block copolymer Tetronic 908 initially provides a composition with particle size that is not at least 50% smaller than the particle size of the composition prepared in the absence of DPPE and Tetronic 908. On subsequent storage at 4° C., the presence of the charged phospholipid DPPE and the block copolymer minimizes subsequent particle growth.

With respect to the data in Table 3.3, particularly lines 1 and 4 relevant to storage at room temperature of a composition containing Ursodiol, the use of charged phospholipid DPPE (see Table 1) together with block copolymer Tetronic 908 initially provides a composition with particle size that is not at least 50% smaller than the particle size of the composition prepared in the absence of DPPE and Tetronic 908. On subsequent storage at room temperature, the presence of the charged phospholipid DPPE and the block copolymer minimizes subsequent particle growth.

With respect to the data in Table 3.4, particularly lines 1 and 4 relevant to storage at 40° C. of a composition containing Ursodiol, the use of charged phospholipid DPPE (see Table 1) together with block copolymer Tetronic 908 initially provides a composition with particle size that is not at least 50% smaller than the particle size of the composition prepared in the absence of DPPE and Tetronic 908. On subsequent storage at 40° C., the presence of the charged phospholipid DPPE and the block copolymer minimizes subsequent particle growth.

With respect to the data in Table 3.6, particularly lines 1 and 4 relevant to storage under thermal cycling of a composition containing Ursodiol, the use of charged phospholipid DMPG (see Table 1) together with block copolymer Tetronic 908 initially provides a composition with particle size that is not at least 50% smaller than the particle size of the composition prepared in the absence of DMPG and Tetronic 908. On subsequent storage under three thermal cycling conditions, the presence of the charged phospholipid DMPG and the block copolymer minimizes subsequent particle growth.

The formulation of Ursodiol prepared with a combination of electrostatic and steric surface modifiers together with the phospholipid surface stabilizer showed good stability under all conditions.

With respect to the data in Table 3.7, particularly lines 1 and 4 relevant to storage at 4° C. of a composition containing Fenofibrate, the use of charged phospholipid DMPG (see Table 1) together with block copolymer Poloxamer 407 initially provides a composition with particle size that is not at least 50% smaller than the particle size of the composition prepared in the absence of DMPG and Poloxamer 407. On subsequent storage at 4° C., the presence of the charged phospholipid DMPG and the block copolymer minimizes subsequent particle growth.

With respect to the data in Table 3.8, particularly lines 1 and 4 relevant to storage at 25° C. of a composition containing Fenofibrate the use of charged phospholipid DMPG (see Table 1) together with block copolymer Poloxamer 407 initially provides a composition with particle size that is not at least 50% smaller than the particle size of the composition prepared in the absence of DMPG and Poloxamer 407. On subsequent storage at 25° C., the presence of the charged phospholipid DMPG and the block copolymer minimizes subsequent particle growth.

With respect to the data in Table 3.9, particularly lines 1 and 4 relevant to storage under shaking conditions of a composition containing Fenofibrate, the use of charged phospholipid DMPG (see Table 1) together with block copolymer Poloxamer 407 initially provides a composition with particle size that is not at least 50% smaller than the particle size of the composition prepared in the absence of DMPG and Poloxamer 407. On subsequent storage under shaking conditions, the presence of the charged phospholipid DMPG and the block copolymer minimizes subsequent particle growth.

With respect to the data in Table 3.10, particularly lines 1 and 4 relevant to storage under thermal cycling conditions of a composition containing Fenofibrate, the use of charged phospholipid DMPG (see Table 1) together with block copolymer Poloxamer 407 initially provides a composition with particle size that is not at least 50% smaller than the particle size of the composition prepared in the absence of DMPG and Poloxamer 407. On subsequent storage under thermal cycling conditions, the presence of the charged phospholipid DMPG and the block copolymer minimizes subsequent particle growth.

The formulation of Fenofibrate prepared with a combination of electrostatic and steric surface modifiers together with the phospholipid surface stabilizer showed good stability under all conditions.

TABLE 3.1

MP Cyclosponne data (5% w/w micronized cyclosporine, 5.5% Mannitol)
Particle size at room temperature

| Sample | w/w % Lipoid E80 | w/w % DMPG | w/w % Pluronic F68 | Initial size (microns) | Final size (microns) | Days |
|---|---|---|---|---|---|---|
| 1 | 10 | 0 | 0 | 2.62 | 8.07 | 66 |
| 2 | 9.5 | 0.5 | 0 | 1.20 | 1.64 | 61 |
| 3 | 9.0 | 0 | 1.0 | 1.77 | 6.74 | 53 |
| 4 | 8.7 | 0.45 | 0.95 | 1.08 | 1.24 | 51 |

TABLE 3.2

MP Ursodiol data (10% w/w Ursodiol, 5.5% Mannitol)
Particle size at 4 C

| Sample | w/w % Lipoid E80 | w/w % DPPE | w/w % Tetronic 908 | Initial size (microns) | Final size (microns) | Days |
|---|---|---|---|---|---|---|
| 1 | 2.4 | 0 | 0 | 1.36 | 1.52 | 30 |
| 2 | 1.6 | 0 | 0.8 | 1.15 | 1.20 | 29 |
| 3 | 2.0 | 0.4 | 0 | 1.34 | 1.33 | 27 |
| 4 | 1.41 | 0.28 | 0.72 | 1.06 | 1.13 | 26 |
| 5 | 0 | 0.4 | 2.0 | 1.37 | 1.34 | 13 |

TABLE 3.3

MP Ursodiol data (10% w/w Ursodiol, 5.5% Mannitol)
Particle size at room temperature

| Sample | w/w % Lipoid E80 | w/w % DPPE | w/w % Tetronic 908 | Initial size (microns) | Final size (microns) | Days |
|---|---|---|---|---|---|---|
| 1 | 2.4 | 0 | 0 | 1.36 | 1.51 | 30 |
| 2 | 1.6 | 0 | 0.8 | 1.15 | 1.19 | 29 |
| 3 | 2.0 | 0.4 | 0 | 1.34 | 1.55 | 29 |
| 4 | 1.41 | 0.28 | 0.72 | 1.06 | 1.13 | 26 |
| 5 | 0 | 0.4 | 2.0 | 1.37 | 1.44 | 24 |

TABLE 3.4

MP Ursodiol data (10% w/w Ursodiol, 5.5% Mannitol)
Particle size at 40 C

| Sample | w/w % Lipoid E80 | w/w % DPPE | w/w % Tetronic 908 | Initial size (microns) | Final size (microns) | Days |
|---|---|---|---|---|---|---|
| 1 | 2.4 | 0 | 0 | 1.36 | 1.51 | 30 |
| 2 | 1.6 | 0 | 0.8 | 1.15 | 1.23 | 29 |
| 3 | 2.0 | 0.4 | 0 | 1.34 | 1.35 | 27 |
| 4 | 1.41 | 0.28 | 0.72 | 1.06 | 1.12 | 26 |
| 5 | 0 | 0.4 | 2.0 | 1.37 | 1.35 | 20 |

TABLE 3.5

MP Ursodiol data (10% w/w Ursodiol, 5.5% Mannitol)
Shaking stability data at room temperature

| Sample | w/w % Lipoid E80 | w/w % DMPG | w/w % Tetronic 908 | Initial size (microns) | Final size (microns) | Days |
|---|---|---|---|---|---|---|
| 1 | 2.4 | 0 | 0 | 1.36 | — | — |
| 2 | 1.6 | 0 | 0.8 | 1.15 | 1.17 | 15 |
| 3 | 2.0 | 0.4 | 0 | 1.34 | 1.36 | 7 |
| 4 | 1.41 | 0.28 | 0.72 | 1.06 | 1.09 | 7 |
| 5 | 0 | 0.4 | 2.0 | 1.37 | 1.37 | 7 |

TABLE 3.6

MP Ursodiol data (10% w/w Ursodiol, 5.5% Mannitol)
Thermal cycling stability data (after 3 cycles)

| Sample | w/w % Lipoid E80 | w/w % DMPG | w/w % Tetronic 908 | Initial size (microns) | Final size (microns) |
|---|---|---|---|---|---|
| 1 | 2.4 | 0 | 0 | 1.36 | — |
| 2 | 1.6 | 0 | 0.8 | 1.15 | 1.21 |
| 3 | 2.0 | 0.4 | 0 | 1.34 | 1.36 |
| 4 | 1.41 | 0.28 | 0.72 | 1.06 | 1.13 |

TABLE 3.7

MP Fenofibrate data (10% w/w Fenofibrate, 5.5% Mannitol)
Particle size at 4 C

| Sample | w/w % Lipoid E80 | w/w % DMPG | w/w % Poloxamer 407 | Initial size (microns) | Final size (microns) | Days |
|---|---|---|---|---|---|---|
| 1 | 4.0 | 0 | 0 | 0.95 | 3.59 | 30 |
| 2 | 3.0 | 0 | 1.0 | 0.86 | 1.10 | 33 |
| 3 | 3.6 | 0.4 | 0 | 0.85 | 2.91 | 33 |
| 4 | 2.77 | 0.31 | 0.92 | 0.82 | 1.17 | 32 |

TABLE 3.8

MP Fenofibrate data (10% w/w Fenofibrate, 5.5% Mannitol)
Particle size at 25 C

| Sample | w/w % Lipoid E80 | w/w % DMPG | w/w % Poloxamer 407 | Initial size (microns) | Final size (microns) | Days |
|---|---|---|---|---|---|---|
| 1 | 4.0 | 0 | 0 | 0.95 | 6.47 | 30 |
| 2 | 3.0 | 0 | 1.0 | 0.86 | 1.32 | 29 |
| 3 | 3.6 | 0.4 | 0 | 0.85 | 8.10 | 29 |
| 4 | 2.77 | 0.31 | 0.92 | 0.82 | 1.39 | 28 |

TABLE 3.9

MP Fenofibrate data (10% w/w Fenofibrate, 5.5% Mannitol)
Shaking stability data

| Sample | w/w % Lipoid E80 | w/w % DMPG | w/w % Poloxamer 407 | Initial size (microns) | Final size (microns) | Days |
|---|---|---|---|---|---|---|
| 1 | 4.0 | 0 | 0 | 0.95 | 3.53 | 8 |
| 2 | 3.0 | 0 | 1.0 | 0.86 | 1.27 | 7 |
| 3 | 3.6 | 0.4 | 0 | 0.85 | 2.86 | 7 |
| 4 | 2.77 | 0.31 | 0.92 | 0.82 | 1.32 | 7 |

TABLE 3.10

MP Fenofibrate data (10% w/w Fenofibrate, 5.5% Mannitol)
Thermal cycling stability data

| Sample | w/w % Lipoid E80 | w/w % DMPG | w/w % Poloxamer 407 | Initial size (microns) | Final size (microns) | # cycles |
|---|---|---|---|---|---|---|
| 1 | 4.0 | 0 | 0 | 0.95 | 3.59 | 3 |
| 2 | 3.0 | 0 | 1.0 | 0.86 | 2.26 | 3 |
| 3 | 3.6 | 0.4 | 0 | 0.85 | 8.61 | 3 |
| 4 | 2.77 | 0.31 | 0.92 | 0.82 | 2.54 | 3 |

The presence of a charged and steric surface modifiers during the formation of micron to sub-micron sized phospholipid coated microparticles provides for the high rate of production of minimally sized particles. Also, the combination of effect of steric and electrostatic stabilizers provides best stability and prevents or minimizes particle growth due to both Ostwald ripening and particle aggregation. Further, charged surface modifiers appear possibly to contribute mostly to particle size reduction whereas steric modifiers contribute mostly to stability.

The above data demonstrate the presence of charged and steric surface modifiers during the formation of micron to sub-micron sized phospholipid coated microparticles provides for a high rate of production of minimally sized particles.

Table 1 lists representative and non-limiting materials useful in this invention. These materials were used in the above examples. Other naturally occurring phospholipids, synthetic phospholipids, and semisynthetic phospholipids are anticipated to be useful in this invention. Other charged surface modifiers and block copolymers are also expected to be useful in this invention. Preferably for use in pharmaceutical compositions, the phospholipids, charged surface modifiers, and block copolymers are biocompatible, nontoxic, and acceptable for use in pharmaceutical compositions.

TABLE 1

Surface Modifiers

| Surface Modifier Name | Abbreviation | Class of surface modifier | Type of stabilization |
| --- | --- | --- | --- |
| Lipoid E-80 | LipE80 | Phospholipid | |
| 1,2-Dimyristoyl-sn-Glycero-3-[Phospho-rac-(1-glycerol)] (Sodium Salt) | DMPG | Charged | Electrostatic |
| 1,2-Dipalmitoyl-sn-Glycero-3-Phosphoethanolamine | DPPE | Charged | Electrostatic |
| Pluronic F127 (also known as Poloxamer 407) | PF127 | Block Copolymer | Steric |
| Tetronic 908 | T908 | Block Copolymer | Steric |
| Pluronic F68 (also known as Poloxomer 188) | PF68 | Block copolymer | Steric |

TABLE 2

List of Suppliers

| Name | Supplier | Location |
| --- | --- | --- |
| Cyclosporine | North China Pharmaceutical Company | China |
| Ursodiol | Tokyo Tanabee | Tokyo, Japan |
| Fenofibrate | Laboratorio Chimico Internazionale s.p.a. | Milan, Italy |
| Lipoid E-80 | Lipoid GMBH | Ludwigshafen, Germany |
| DMPG, DPPE | Avanti Polar Lipids | Alabaster, Alabama, USA |
| Tetronic and Pluronic Block Polymers | BASF | Mount Olive, New Jersey, USA |

The formulations described in this invention can be suspensions of microparticles, for example suspensions of microparticles in an aqueous medium. These suspensions are wet suspensions of microparticles according to this invention. Preferably, the formulations are suitable for use as pharmaceutical formulations for the treatment of disease states in humans or animals. The wet suspensions can be converted to dry powders, for example by lyophilization or spray drying or evaporation of the water or other technique useful for the removal of the liquid portion of the formulation. The dry powders can be converted into other dosage forms such as tablets and capsules, ointments and creams, suppositories, pessaries, lozenges, or other dosage forms for administration to human or animal patients for use in therapeutic applications of the drug. Alternatively, the dry powders can be resuspended or redispersed in suitable liquids such as water, sterile water, saline solution, phosphate buffered saline, water for injection, and the like to form suspensions of the microparticles that can be administered to human or animal patients for use in therapeutic applications of the drug.

Routes of administration of the microparticles of this invention as wet suspensions or as dry powders or as dosage forms derived from the wet suspensions or dry powders include commonly used modes of treatment such as oral delivery, nasal delivery, transdermal delivery, inhalation by aspiration, dissolution in the mouth or other body cavity, injection into vessels, injection into tissues, injection or deposition into cavities in the body, injection into organs, and the like in a body undergoing treatment with the drug in the microparticle.

What is claimed is:

1. A pharmaceutical composition comprising electrostatic and steric-stabilized particles having volume weighted mean particle size diameters of about 0.05 to about 10 microns of a water-insoluble or poorly soluble drug, said particles having phospholipid coated surfaces and being stabilized with a combination of a highly purified charged phospholipid surface modifier an d a block copolymer of ethylene oxide and propylene oxide, wherein the volume weighted mean particle size diameter of said particles is greater than 50% but less than 100% of the volume weighted mean particle size diameter of particles comprising said poorly soluble drug and said phospholipid coated surfaces prepared by otherwise identical means in the absence of said combination of highly purified charged phospholipid surface modifier and block copolymer of ethylene oxide and propylene oxide, and wherein the highly purified charged phospholipid surface modifier provides electrostatic stabilization and the block copolymer of ethylene oxide and propylene oxide provides steric stabilization that minimize particle size growth caused by Ostwald ripening and particle aggregation and provides for small particle formation.

2. A pharmaceutical composition comprising electrostatic and steric-stabilized particles having volume weighted mean particle size diameters of about 0.05 microns to about 10 microns of a water-insoluble or poorly soluble drug, the particles coated with a mixture of 0.01% to 50% wt naturally occurring phospholipids, 0.01 to 5.0% wt of a highly purified charged phospholipid surface modifier and 0.01 to 20% wt of a block copolymer of ethylene oxide and propylene oxide, wherein the volume weighted mean particle size diameter of said particles is greater than 50% but less than 100% of the volume weighted mean particle size diameter of particles comprising said poorly soluble drug and said naturally occurring phospholipids prepared by otherwise identical means in the absence of both said highly purified charged phospholipid surface modifier and said block copolymer of ethylene oxide and propylene oxide, and wherein the highly purified charged phospholipid surface modifier provides electrostatic stabilization and the block copolymer of ethylene oxide and propylene oxide provides steric stabilization that minimize particle size growth caused by Ostwald ripening and particle aggregation and provides for small particle formation.

3. The composition of claims 1 or 2 wherein the block copolymer is derived from ethylene oxide and propylene oxide, or a tetrafunctional block copolymer derived from sequential addition of ethylene oxide and propylene oxide to ethylene diamine or combinations thereof.

4. The composition of claim 1 or 2 wherein the phospholipid is a phospholipid of egg or plant origin or semisynthetic or synthetic in partly or fully hydrogenated form or in a desalted or salt form.

5. The composition of claim 2 wherein the naturally occurring phospholipid is present in an amount of 0.05% to 20% wt.

6. The composition of claim 1 or 2 wherein the highly purified charged phospholipid surface modifier is selected from phosphatidylcholine, dimyristoyl phosphatidylglycerol sodium salt, phosphatidyl ethanolamine, phosphatidylserine, phosphatidic acid, or combinations thereof.

7. The composition of claim 6 wherein the highly purified charge phospholipid surface modifier is present in an amount of 0.05% to 1.0% wt.

8. The composition of claim 3 wherein the block copolymer is present in an amount of 0.1% to 10%.

9. The pharmaceutical composition of claim 1 or 2 in sterile, injectable form for intravenous, intra-arterial, intramuscular, intradermal, subcutaneous intra-particular, cerebrospinal, epidural, intracostal, intraperitoneal, intratumor, intrabladder, intra-lesion or subconjunctival administration.

10. A suspension, spray-dried powder, lyophilized powder granules or tablets of the composition of claim 1 or 2.

11. A hard or soft gel capsule formulation comprising the composition of claim 1 or 2.

12. A pharmaceutical composition comprising a powder of electrostatic and steric-stabilized particles having volume weighted mean particle size diameters of about 0.05 microns to about 10 microns of a water-insoluble or poorly soluble drug, the particles coated with a mixture of 0.01% to 50% wt naturally occurring phospholipids, 0.01 to 5.0% wt of a highly purified charged phospholipid surface modifier and 0.01 to 20% wt of a block copolymer of ethylene oxide and propylene oxide, wherein the volume weighted mean particle size diameter of said particles is greater than 50% but less than 100% of the volume weighted mean particle size diameter of particles comprising said poorly soluble drug and said naturally occurring phospholipids prepared by otherwise identical means in the absence of both said highly purified charged phospholipid surface modifier and said block copolymer of ethylene oxide and propylene oxide, and wherein the highly purified charged phospholipid surface modifier provides electrostatic stabilization and the block copolymer of ethylene oxide and propylene oxide provides steric stabilization that minimize particle size growth caused by Ostwald ripening and particle aggregation and provides for small particle formation.

* * * * *